US008974363B2

(12) United States Patent
Dees et al.

(10) Patent No.: US 8,974,363 B2
(45) Date of Patent: Mar. 10, 2015

(54) TOPICAL MEDICAMENTS AND METHODS FOR PHOTODYNAMIC TREATMENT OF DISEASE

(75) Inventors: H. Craig Dees, Knoxville, TN (US); Timothy C. Scott, Knoxville, TN (US); John Smolik, Loudon, TN (US); Eric A. Wachter, Oak Ridge, TN (US); Walter G. Fisher, Knoxville, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 721 days.

(21) Appl. No.: 11/936,963

(22) Filed: Nov. 8, 2007

(65) Prior Publication Data

US 2008/0118578 A1 May 22, 2008

Related U.S. Application Data

(63) Continuation-in-part of application No. 09/635,276, filed on Aug. 9, 2000, now abandoned, which is a continuation-in-part of application No. 08/989,231, filed on Dec. 11, 1997, now Pat. No. 5,998,597, and a continuation-in-part of application No. 09/130,041, filed on Aug. 6, 1998, now abandoned, and a continuation-in-part of application No. 09/184,388, filed on Nov. 2, 1998, now Pat. No. 6,493,570, and a continuation-in-part of application No. 09/216,787, filed on Dec. 21, 1998, now Pat. No. 6,331,286.

(60) Provisional application No. 60/149,015, filed on Aug. 13, 1999.

(51) Int. Cl.
*A61K 31/352* (2006.01)
*A61K 33/14* (2006.01)
*A61K 41/00* (2006.01)

(52) U.S. Cl.
CPC ............... *A61K 31/352* (2013.01); *A61K 33/14* (2013.01); *A61K 41/00* (2013.01)
USPC ............... 600/2; 424/678; 424/680; 514/453; 514/454

(58) Field of Classification Search
CPC . A61K 2300/00; A61K 31/352; A61K 33/14; A61K 41/00; A61K 9/0019; A61K 41/0038; H01R 9/26
USPC ................ 424/678, 680; 600/2; 514/453, 454
See application file for complete search history.

(56) References Cited

U.S. PATENT DOCUMENTS

| | | |
|---|---|---|
| 3,563,750 A | 2/1971 | Walker et al. |
| 3,868,950 A | 3/1975 | Kato |
| 3,973,848 A | 8/1976 | Jowett et al. |
| 3,986,513 A | 10/1976 | Stuhl |
| 4,066,650 A | 1/1978 | Egyud |
| 4,172,979 A | 10/1979 | Morrison |
| 4,241,060 A | 12/1980 | Smithen |
| 4,282,232 A | 8/1981 | Agrawal |
| 4,320,140 A | 3/1982 | Crounse et al. |
| 4,371,540 A | 2/1983 | Lee et al. |
| 4,444,189 A | 4/1984 | Seiverd |
| 4,462,992 A | 7/1984 | Agrawal et al. |
| 4,490,543 A | 12/1984 | Berquist et al. |
| 4,578,079 A | 3/1986 | Ruoslahti et al. |
| 4,589,881 A | 5/1986 | Pierschbacher et al. |
| 4,599,227 A | 7/1986 | Dees et al. |
| 4,647,578 A | 3/1987 | Crounse et al. |
| 4,652,562 A | 3/1987 | Berenyi nee Poldermann |
| 4,681,091 A | 7/1987 | Picker et al. |
| 4,691,332 A | 9/1987 | Burstein et al. |
| 4,769,390 A | 9/1988 | Roelz et al. |
| 4,820,258 A | 4/1989 | Mondain-Monval |
| 4,822,335 A | 4/1989 | Kawai et al. |
| 4,846,789 A | 7/1989 | Heitz et al. |
| 4,856,528 A | 8/1989 | Yang et al. |
| 4,867,973 A | 9/1989 | Goers et al. |

(Continued)

FOREIGN PATENT DOCUMENTS

| | | |
|---|---|---|
| EP | 0049837 A1 | 4/1982 |
| EP | 0146059 A2 | 6/1985 |

(Continued)

OTHER PUBLICATIONS

Andreoni, A., et al., (1982) Two-step lazer activation of hematoporphyrin derivative. Chem. Phys. Lett. 8 8, 37-39.
Bodaness, R.S. and King, D.S. (1985) The two-photon induced fluorescence of the tumor localizing photo-sensitizer hematoporphyrin derivative via 1064 rm . . . Biochem. Biophys.
Bodaness, R.S., et al., (1986) Two-photon laser-induced fluorescence of the tumor-localizing photosensitive hematoporphyrin derivative. J. Biol. Chem. 2 6 1, 12098-12101.
Chan, C.K. and Sari, S.O. (1974) Tunable dye laser pulse converter for production of picosecond pulses. App. Phys. Lett. 2 5, 403-406.
Cheong, W-F. et al., "A Review of the Optical Properties of Biological Tissues," IEEE 5.Quant. Election 2 6, 2166-2185 (1990).

(Continued)

*Primary Examiner* — Janet Epps-Smith
(74) *Attorney, Agent, or Firm* — Husch Blackwell LLP

(57) ABSTRACT

New photodynamic, topically-applicable medicaments and certain medical uses of such photodynamic medicaments for treatment of human or animal tissue are described, wherein a primary active component of such medicaments is a halogenated xanthene. The halogenated xanthenes constitute a family of potent photosensitizers that become photoactivated upon illumination of the treatment site with visible wavelengths of light. In preferred embodiments, such medicaments are used for treatment of a variety of conditions affecting the skin and related organs; the mouth and digestive tract and related organs; the urinary and reproductive tracts and related organs; the respiratory tract and related organs; various other internal or external tissue surfaces, such as tissue surfaces exposed during surgery; and for treatment of a variety of conditions related to microbial or parasitic infection. In another preferred embodiment, such medicaments are produced in various formulations including liquid, semisolid or aerosol delivery vehicles.

22 Claims, 2 Drawing Sheets

(56) References Cited

U.S. PATENT DOCUMENTS

| | | | |
|---|---|---|---|
| 4,880,821 A | 11/1989 | Saari | |
| 4,897,423 A | 1/1990 | Saari et al. | |
| 4,915,804 A | 4/1990 | Yates et al. | |
| 4,921,589 A | 5/1990 | Yates et al. | |
| 4,921,963 A | 5/1990 | Skov et al. | |
| 4,925,736 A | 5/1990 | Shikowitz | |
| 4,927,941 A | 5/1990 | Kagiya et al. | |
| 4,945,102 A | 7/1990 | Suzuki et al. | |
| 4,954,515 A | 9/1990 | Suto | |
| 4,957,481 A | 9/1990 | Gatenby | |
| 4,973,848 A | 11/1990 | Kolobanov et al. | |
| 4,977,273 A | 12/1990 | Kagiya et al. | |
| 4,983,670 A | 1/1991 | Yates et al. | |
| 5,008,907 A | 4/1991 | Norman et al. | |
| 5,019,368 A | 5/1991 | Epstein et al. | |
| 5,026,694 A | 6/1991 | Skov et al. | |
| 5,034,613 A | 7/1991 | Denk et al. | |
| 5,036,089 A | 7/1991 | Suto | |
| 5,036,096 A | 7/1991 | Suto | |
| 5,053,006 A | 10/1991 | Watson | |
| 5,064,849 A | 11/1991 | Suzuki et al. | |
| 5,128,139 A | 7/1992 | Brown et al. | |
| 5,147,652 A | 9/1992 | Egyud | |
| 5,149,801 A | 9/1992 | Kahl et al. | |
| 5,151,096 A | 9/1992 | Khoury | |
| 5,175,287 A | 12/1992 | Lee et al. | |
| 5,215,738 A | 6/1993 | Lee et al. | |
| 5,219,346 A | 6/1993 | Wagnieres et al. | |
| 5,225,182 A | 7/1993 | Sharma | |
| 5,231,984 A | 8/1993 | Santana-Blank | |
| 5,258,453 A | 11/1993 | Kopecek et al. | |
| 5,270,330 A | 12/1993 | Suzuki et al. | |
| 5,284,831 A | 2/1994 | Kahl et al. | |
| 5,294,715 A | 3/1994 | Papadopoulou-Rosenzweig et al. | |
| 5,302,369 A | 4/1994 | Day et al. | |
| 5,304,654 A | 4/1994 | Kagiya et al. | |
| 5,342,959 A | 8/1994 | Beylin et al. | |
| 5,354,774 A | 10/1994 | Deckelbaum et al. | |
| 5,368,031 A | 11/1994 | Cline et al. | |
| 5,409,483 A | 4/1995 | Campbell et al. | |
| 5,445,608 A | 8/1995 | Chen et al. | |
| 5,457,183 A | 10/1995 | Sessler et al. | |
| 5,462,053 A | 10/1995 | Briggs et al. | |
| 5,468,234 A | 11/1995 | Griffin et al. | |
| 5,481,000 A | 1/1996 | Beylin et al. | |
| 5,498,694 A | 3/1996 | Ruoslahti | |
| 5,514,707 A | 5/1996 | Deckelbaum et al. | |
| 5,543,527 A | 8/1996 | Beylin et al. | |
| 5,552,452 A | 9/1996 | Khadem et al. | |
| 5,556,992 A | 9/1996 | Gaboury et al. | |
| 5,558,666 A | 9/1996 | Dewey et al. | |
| 5,567,765 A | 10/1996 | Moore et al. | |
| 5,571,152 A | 11/1996 | Chen et al. | |
| 5,575,756 A | 11/1996 | Karasawa et al. | |
| 5,576,013 A * | 11/1996 | Williams et al. | 424/423 |
| 5,579,773 A | 12/1996 | Vo-Dinh et al. | |
| 5,586,981 A | 12/1996 | Hu | |
| 5,590,660 A | 1/1997 | MacAulay et al. | |
| 5,591,422 A | 1/1997 | Hemmi et al. | |
| 5,599,923 A | 2/1997 | Sessler et al. | |
| 5,601,802 A | 2/1997 | Hemmi et al. | |
| 5,602,142 A | 2/1997 | Papadopoulou-Rosenzweig et al. | |
| 5,616,584 A | 4/1997 | Lee et al. | |
| 5,622,699 A | 4/1997 | Ruoslahti et al. | |
| 5,622,946 A | 4/1997 | Sessler et al. | |
| 5,624,925 A | 4/1997 | Lee et al. | |
| 5,627,263 A | 5/1997 | Ruoslahti et al. | |
| 5,629,291 A | 5/1997 | Ruoslahti et al. | |
| 5,632,970 A | 5/1997 | Sessler et al. | |
| 5,641,764 A | 6/1997 | Martin et al. | |
| 5,645,816 A | 7/1997 | Unger | |
| 5,647,368 A | 7/1997 | Zeng et al. | |
| 5,654,267 A | 8/1997 | Vuori et al. | |
| 5,654,423 A | 8/1997 | Kahl et al. | |
| 5,659,048 A | 8/1997 | Beylin et al. | |
| 5,667,764 A | 9/1997 | Kopia et al. | |
| 5,674,183 A | 10/1997 | Adachi | |
| 5,676,928 A | 10/1997 | Klaveness et al. | |
| 5,693,015 A | 12/1997 | Walker et al. | |
| 5,700,825 A | 12/1997 | Hofer et al. | |
| 5,702,683 A | 12/1997 | Smith et al. | |
| 5,706,810 A | 1/1998 | Rubinsky et al. | |
| 5,709,653 A | 1/1998 | Leone | |
| 5,728,090 A | 3/1998 | Martin et al. | |
| 5,733,572 A | 3/1998 | Unger et al. | |
| 5,747,064 A | 5/1998 | Burnett et al. | |
| 5,773,460 A | 6/1998 | Gaboury et al. | |
| 5,780,052 A | 7/1998 | Khaw et al. | |
| 5,780,653 A | 7/1998 | Tao et al. | |
| 5,807,231 A | 9/1998 | Liprie | |
| 5,827,186 A | 10/1998 | Chen | |
| 5,829,448 A | 11/1998 | Fisher et al. | |
| 5,830,526 A | 11/1998 | Wilson et al. | |
| 5,832,931 A | 11/1998 | Wachter et al. | |
| 5,913,884 A | 6/1999 | Trauner et al. | |
| 5,935,942 A | 8/1999 | Zeimer | |
| 5,998,597 A | 12/1999 | Fisher et al. | |
| 6,036,941 A * | 3/2000 | Bottiroli et al. | 424/9.6 |
| 6,042,603 A | 3/2000 | Fisher et al. | |
| 6,331,286 B1 | 12/2001 | Dees et al. | |
| 7,384,623 B1 * | 6/2008 | Dees et al. | 424/9.37 |
| 7,390,668 B2 * | 6/2008 | Dees et al. | 436/124 |
| 7,648,695 B2 * | 1/2010 | Dees et al. | 424/9.37 |

FOREIGN PATENT DOCUMENTS

| | | |
|---|---|---|
| EP | 0175617 A | 3/1986 |
| EP | 0504761 A1 | 9/1992 |
| EP | 0471794 B1 | 10/1996 |
| EP | 0631610 B1 | 6/1997 |
| EP | 0652709 B1 | 3/1999 |
| JP | 11-92360 | 4/1999 |
| WO | WO 90/13296 | 11/1990 |
| WO | WO 93/21992 | 11/1993 |
| WO | WO 95/02324 A | 1/1995 |
| WO | WO 96/07431 | 3/1996 |
| WO | WO 97/03697 | 2/1997 |
| WO | WO 97/26920 | 7/1997 |
| WO | WO 97/39064 A1 | 10/1997 |
| WO | WO 98/22184 | 5/1998 |
| WO | WO 00/07515 A | 2/2000 |
| WO | WO 00/25665 A | 5/2000 |
| WO | WO 00/25819 | 5/2000 |
| WO | WO 00/25829 | 5/2000 |
| WO | WO 00/37927 A | 6/2000 |

OTHER PUBLICATIONS

Cimino., G.D., et al., (1985) Psoralens as photoactive probes of nucleic acid structure and function: organic chemistry, photochemistry, and biochemistry. Ann. Rev. Biochem.

Dagani, R., (1996) Two photons shine in 3-D data storage. Chem Eng. News, Sep. 23, 1996, 68-70.

Dougherty, T.J., et al., "Photoradiation Therapy II Cure of Animal Tumors With Hematoparphyrin and Light," J.Nat'l Cancer-Inst. 5 5, 115-120 (1975).

Dolphin, D., (1994) 1993 Syntex award lecture, photomedicine and photodynamic therapy. Can. J. Chem. 7 2 1005-1013.

Draumer, N.H., et al., (1997) Femtosecond dynamics of excited-state evolution in [Ru(bpy)3]2+. Science 2 7 5, 54-57.

Fisher, W.G., et al., (1997) Two-photon spectroscopy and photochemistry of tris (2,2'-bipyridine)-0ruthenium(II). J. Phys. Chem. (in press).

Fugishima, I., et al., (1991) Photodynamic therapy using phophorbide a and ND:YAG laser. Neurol. Med. Chir. (Tokyo) 3 1, 257-263.

Georges, J., et al., (1996) Limitations arising from optical saturation in fluorescence and thermal lens spectrometries using . . . App. Spectrosc. 5 0, 1505-1511.

Gomer, C.J., et al., (1989) Properties and applications of photodynamic therapy. Rad. Res. 1 2 0, 1-18.

Göpert-Mayer, M., (1931) Elementary process with two quantum jumps. Ann. Physik 9, 273-294.

(56) References Cited

OTHER PUBLICATIONS

Hammer, D.X., et al., (1996) Experimental investigation of ultrashort pulse laser-induced breakdown thresholds in aqueous media. Ieee J. Quant. Electron. 3 2, 670-678.
Harris, J.M., et al., (1975) Pulse generation in cw-dye laser by mode-locked synchronous pumping. App. Phys. Lett. 2 6, 16-18.
Hermann, J.P. and Ducuing, J. (1972) Dispersion of the two-photon cross section in thodamine dyes. Opt. Comm. 6, 101-105.
Inaba, H., et al., (1985) Nd:YAG laser-induced hematoporphyrin visible fluorescence and two photon-excited . . . J. Opt. Soc. Am. A:Opt. Inage Science 2, P72 (mtg abst).
Kaiser, W. and Garrett, C.G.B., (1961) Two photon excitation in $CaF_2:Eu^{2+}$. Phys. Rev. Lett. 7, 2929-231.
Kennedy, S.M. and Lytle, F.E. (1986) p-Bis (o-methylstryl) benzene as a power-squared sensor for two-photon absorption measurement between 537 and 694 rm. Anal. Chem. 5 8, 26.
Kessel, D., et al., (1991) Photophysical and photobiological properties of diporphyrin ethers. Photochem. Photobiol. 5 3, 469,474.
Lenz, P. (1995) In vivo excitation of photosensitizers by infrared light. Photochem. Photobiol. 6 2, 333-338.
Lytle, F.E., (1981) Laser fundamentals. In Lasers in Chemical Analysis (Ed.: G.M.Hieftje,et al.) 5-6. The Humana Press, New Jersey.
Lytle, F.E., et al., (1980) Two-photon excitation of polycyclic aromatic hydrocarbons. Intern. UJ. Environ. Anal. Chem. 8, 303-312.
Marchesini, R., et al., (1986) A study on the possible involvement of nonlinear mechanism of light absorption by HpD with Nd:YAG laser. Lasers Surg. Med. 6, 323-327.
Mashiko, D., et al., (1985) Basic study on photochemical effect of pheophorbide-a irradiated by Nd:YAG laser light. Nippon Laser Igakukaishi 6, 113-116.
Mashiko, S., et al., (1986) Two-photon excited visible fluorescence of hematoporphyrin and phiophorbide a and in vitro experiments of the photodynamic . . . J. Opt. Soc. Am. B:Opt.
McClain, W.M., (1974) Two-photon molecular spectroscopy. Acc. Chem. Res. 7 129-135.
McClain, W.M. (1971) Excited state symmetry assignment through polarized two-photon absorption studies of fluids. J. Chem. Phys. 5 5, 2789-2796.
Mello, R.S., et al., "Radiation Dose Enhancement in Tumors with Iodine," Medical Physics, vol. 1, No. 1, pp. 75-78, Jan./Feb. 1983.
Monson, P.R. and McClain, W.M. (1970) Polarization dependence of the two-photon absorption of tumbling molecules . . . J. Chem. Phys. 5 3, 29-37.
Moscatelli, F.A., (1985) a Simple Conceptual Model for Two-Photon Absorption. Am. J. Phys. 5 4, 52-54.
Niemz, M.H., (1995) Threshold dependence of laser-induced optical breakdown on pulse duration. Appl. Phys. Lett. 6 6, 1181-1183.
Norman, A., et al., "X-Ray Phototherapy for Canine Brain Masses," Radiation Oncology Investigations, vol. 5, pp. 8-14, 1997.
Oh, D.H., et al., (1997) Two-photon excitation of 4'-hydroxymethyl-4,5', 8-trimethylpsoralen. Photochem. Photobiol. 6 5, 91-95.
Patrice, T., et al., (1983) Neodymium-yttrium aluminum garnet laser destruction of nonsensitized and hematoporphyrin derivative-sensitized tumors. Canc. Res. 4 3, 2876-2879.
Peticolas, W.L., (1967) Multiphoton spectroscopy. Ann. Rev. Phys. Chem. 1 8, 233-260.
Prasad, P.N. and He, G.S., (1996) Multiphoton resonant nonlinear-optical processes in organic molecules ACS Symposium Series 6 2 8, 225-236.
Shea, C.R., et al., (1990) Mechanistic investigation of doxycyckine photosensitization by picosecond-pulsed . . . J. Biol. Chem. 2 6 5, 5977-5982.
Song, P.S. and Tapley, K.J., Jr. (1979) Photochemistry and photobiology of psoralens. Photochem. Photobiol. 2 9, 1177-1197.
Spence, D.E., et al., (1991) 60-fsec pulse generation from a self-mode-locked Ti:Sapphire laser. Opt. Lett. 1 6, 42-44.
Steil, H., et al., (1993) Photophysical properties of the photosensitizer phophorbide a studied at high photon flux densities. J. Photochem. Photobiol. B: Biology 1 7, 181-18.
Supplementary Partial European Search Report dated Apr. 23, 2004.
Swofford, R.L. and McClaim, W.M., 1975) The effect of spatial and temporal laser beam characteristics on two-photon absorption. Chem. Phys. Lett. 3 4, 455-459.
United States Statutory Invention Registration No. H505 to Slatkin et al., for Boron Uptake in Tumors, Cerebrum and Blood From [10B]$NA_4B_{24}H_{22}S_2$, published Aug. 2, 1988.
Wachter, E.A., Fisher et al., "Titanium: Sapphire Laser as an Excitation Source in Two-Photon Spectroscopy," Applied Spectroscopy, vol. 51, No. 2, pp. 218-226 (1997).
Wilson, B.C. and Patterson, M.S., (1986) The physics of photodynamic therapy. Phys. Med. Biol. 3 1, 327-360.
Yamashita, Y., et al., (1991) Photodynamic therapy using pheophorbide-a and Q-switched Nd:YAG laser on implanted human hepatocellular carcinoma. Gast. Jap. 2 6, 623-627.
Kaf. Kozhn. Ven. Bol., II Med. Inst., Moscow, Treatment of psoriasis with ultraviolet irradiation in combination with 1% alcohol solution of eosin, Elsevier Science B.V., Amsterdam, vol. 54, pp. 70-72 (1978).
Prakash C. Joshi, Ph.D and Madhu A. Pathak, M.B. M.S., Ph.D., "The Role of Active Oxygen ($^1O_2$ and $O_2$) Induced by Crude Coal Tar and its Ingredients Used in Photochemotherapy of Skin Diseases", vol. 82, No. 1, pp. 1-7 (1984).
Wachter, E. et al., Imaging Photosensitizer Distribution and Pharmacology using Multiphoton Microscopy, Functional Imaging and Optical Manipulation of Living Cells and Tissues, SPIE Paper 4622A-14, BiOS 2002 (Biomedical Optics), San Jose, CA 24, Jan. 2002.
Boehncke, W.-H. et al, "Treatment of Psoriasis by Topical Photodynamic Therapy with Polychromatic Light," The Lancet, vol. 343, Mar. 26, 1994, p. 801.
Levy, J.G., "Photodynamic Therapy," Trends in Biotechnology, vol. 13, No. 1, 1995, pp. 14-18.
Bissonnette, R. et al, "Current Status of Photodynamic Therapy in Dermatology," Dermatologic Clinics, vol. 15, No. 3, Jul. 1997, pp. 507-519.
Office Action re Japanese application No. JP 2001-516527, dated May 13, 2014 (with English translation).
U.S. Appl. No. 09/382,622, filed Aug. 25, 1999, Dees.
U.S. Appl. No. 09/799,785, filed Mar. 6, 2001, Dees.
U.S. Appl. No. 09/817,448, filed Mar. 26, 2001, Dees.
U.S. Appl. No. 09/900,355, filed Jul. 6, 2001, Dees.
U.S. Appl. No. 10/331,854, filed Dec. 30, 2002, Dees.
U.S. Appl. No. 10/999,313, filed Nov. 30, 2004, Dees.
U.S. Appl. No. 11/124,654, filed May 9, 2005, Dees.
Amato, "Hope for a Magic Bullet That Moves at the Speed of Light," Science 262:32-33, (1993).
Aungst, B.J., "Fatty Acids as Skin Permeation Enhancers," Percutaneous Penetration Enhancers, 1995, pp. 277-287, CRC Press, Inc., Boca Raton, FL.
Barr, H., et al., "Eradication of High-Grade Dysplasia in Columnar-Lined (Barrett's) Oesophagus by Photodynamic Therapy with Endogenously Generated Protoporphyrin IX," Lancet, (1996).
Bays, et al., "Light Dosimetry for Photodynamic Therapy in the Esophagus," Lasers in Surgery & Medicine, vol. 20, 290-303, 1997.
Bernhard, E.J., et al., "Re-Evaluating Gadolinium(III) Texaphyrin as a Radiosensitizing Agent," Cancer Research, vol. 60, pp. 86-91, Jan. 2000.
Bezman, et al., "Photodynamic Inactivation of *E. Coli* by Rose Bengal Immobilized on Polystyrene Beads," Photochemistry and Photobiology, vol. 28, pp. 325-329 (1978).
Biddlestone, et al., "The Histopathology of Treated Barrett's Esophagus," AM J Surg Pathol, vol. 22, No. 2, 239-245, 1998.
Bottiroli, G., Croce, AC, Enzyme-Assisted Cell Photosensitization, Photochem Photobiol Sep. 1997; 66(3):374-83.
Budavari, S., ed., et al., The Merck Index, Merck & Co., Inc., 11th Ed., p. 4943, 1989.
Castro, et al., "The Concept of Laser Phototherapy," Laser Applications in Otolaryngology 29(b):1011-29, (1996).
Chattaraj, S.C. and Walker, R.B., "Penetration Enhancer Classification," Percutaneous Penetration Enhancers, 1995, pp. 5-20, CRC Press.

(56) References Cited

OTHER PUBLICATIONS

Chen, Sun-Yung, et al., "Theory of Two-Photon Induced Fluorescence Anisotropy Decay in Membranes," Biophys. J. Biophysical Society, vol. 64, pp. 1567-1575 (May 1993).
Definition of "Photodynamic," Merriam-Webster Dictionary, electronic edition, http://www.m-w.com/cgi-bin/dictionary, printed Sep. 4, 2003.
Definition of "Photosensitize," Merriam-Webster Dictionary, electronic edition, http:/www.m-w.com/cgi-bin/dictionary, printed Sep. 30, 2003.
Delpat, et al., "A New Liver Function Test: The Elimination of Rose Bengal When Injected Into the Circulation of Human Subjects," Arch. Intern. Med., vol. 34, pp. 533-541,1924.
Engelstad, et al., "Contrast Agents," Magnetic Resonance Imaging, Chapter 9, pp. 161-181, 215-219 (1988).
Ferguson, et al., "Resection for Barrett's Mucosa with High-Grade Dysplasia: Implications for Prophylactic Photodynamic Therapy," Journal of Thoracic & Cardiovascular Surgery, (1997).
Fisher, et al., "Clinical and Preclinical Photodynamic Therapy," Lasers in Surgery and Medicine, vol. 17, pp. 2-31, 1995.
Fluhler, et al., "Laser Intensity and Wavelength Dependence of Rose-Bengal-Photosensitized Inhibition of Red Blood Cell Acetylcholinesterase," Biochemica et Biophysica Acta, (1989); 990(3), pp. 269-275.
Hearst, J.E., et al., "The Reaction of the Psoralens with Deoxyribonucleic Acid," Quarterly Review of Biophysics, 17 (1984) 1-44.
http://eosweb.larc.nasa.gov/EDDOCS/Wavelengths_for_Colors. html; (2006) Responsible NASA Official: Michelle T. Ferebee.
Huang, et al., "Photothrombosis of Corneal Neovascularization by Intravenous Rose Bengal and Argon Laser Irradiation," Arch Opthalmol., vol. 106, pp. 680-685 (1988).
International Search Report for Application No. PCT/US99/17515, dated Oct. 25, 1999.
Iwamoto, K.S., et al., "Radiation Dose Enhancement Therapy with Iodine in Rabbit VX-2 Brain Tumors," Radiation Therapy and Oncology, vol. 8, pp. 161-170, 1987.
Johnson, Philip M., "The Multiphoton Ionization Spectrum of Benzene," Journal of Chemical Physics, vol. 64, No. 10, 4143-4148 (May 1976).
Joshi, et al., "The Role of Active Oxygen (1O2 and O2) Induced by Crude Coal Tar and its Ingredients Used in Photochemotherapy of Skin Diseases," 1984.
Katsumi, et al., "Photodynamic Therapy with a Diode Laser for Implanted Fibrosarcoma in Mice Employing Mono-L-Aspartyl Chlorin E6", Photochemistry and Photobiology (1996).
Kennedy, J.C., et al., "Photodynamic Therapy With Endogenous Protoporphyrin IX: Basic Principles and Present Clinical Experience," J. of Photochemistry and Photobiology, B: B, 1990, 6(1-2), pp. 143-148.
Kozhn, Kaf. Ven. Bol., II Med. Inst., Moscow, Treatment of psoriasis with ultraviolet irradiation in combination with 1% alcohol solution of eosin, Elsevier Science B.V., Ams, (1978).
Kung-Tung, et al., "Therapeutic Effects of Photosensitizer in Combination with Laser and ACNO on an in Vivo or in Vitro Model of Celebral Glioma," Chinese Medical Journal 108(, (1995).
Kurebayahi, et al. (English Translation of Abstract) The Journal of Toxicological Sciences, May 1988. vol. 13. No. 2, pp. 61-70.
Lakowicz, Joseph R., et al., "Two-Color Two-Photon Excitation of Fluorescence," Photochemistry and Photobiology, pp. 632-635 (1996).
Lauffer, et al., "MRI Contrast Agents: Basic Principles and Organ- and Tissue-Directed MRI Contrast Agents," MRI Clinical Magnetic Resonance Imaging, Second Edition, vol. O, (1996).
Lindman, et al., "General Properties of Halogens and Static Parameters," Chlorine, Bromine and Iodine NMR—Physioco-Chemical and Biological Applications, pp. 1-5 (1976).
Marcus, et al., "Photodynamic Therapy for the Treatment of Squamous Cell Carcinoma Using,Benzoporphyrin Derivative," J. Dermatol Sung Oncol 20:375-382, (1994).

Matsudaira, H., et al., "Iodine Contrast Medium Sensitizes Cultured Mammalian Cells to X Rays but not to Gamma Rays," Radiation Research, vol. 84, pp. 144-148, 1980.
Merck Index, 12th edition, 1996, entry Nos. 5055, 5068, 5069 and 5071.
Miller, R.W., at al., "Evaluation of Incorporated Iododeoxyuridine Cellular Radiosensitization by Photon Activation Therapy," Int. J. Radiation Oncology, Biol. Phys., vol. 13, (1987).
Neckers, D.C., Rose Bengal, Journal of Photochemistry and Photobiology, A: Chemistry: 47, pp. 1-29 (1989).
Nieman, George C., et al., "A New Electronic State of Ammonia Observed by Multiphoton Ionization," J. Chem. Phys. 68(12), pp. 5656-5657 (1978).
Norman, A., et al., "Iodinated Contrast Agents for Brain Tumor Localization and Radiation Dose Enhancement," Invest. Radiol., vol. 26, pp. s120-s1221, 1991.
Norman, A., et al., "Point/Counterpoint: Radiation Doses in Radiation Therapy are not Safe," Med. Phys. vol. 24 (11), pp. 1710-1713, Nov. 1997.
Norman, A., et al., "X-Ray Phototherapy for Solid Tumors," Aced Radiol, vol. 5, (Suppl 1), pp. s177-s179, Apr. 1998.
Overholt, et al., "Photodynamic Therapy for Barrett's Esophagus: Clinical Update," AJG, vol. 91, No. 9, 1719-1723, 1996.
Overholt, et al., "Photodynamic Therapy for Barrett's Esophagus: Cardiac Effects," Lasers in Surgery & Medicine, vol. 21, No. 5, 824-829, Nov. 1997.
Paddock Laboratories, Inc., "Paddock Compounding Vehicles," pp. 1-3, http://www.paddocklabs.com/compound/vehiclbb.html, 1997.
Pfeffer, W.D., et al., "Laser Two-Photon Excited Fluorescence Detector for Microbore Liquid Chromatography," Analytical Chemistry, 58 (1986) 2103-2105.
The Photonics Dictionary 2000, Book 4, 46th Edition, pp. D-105 and D-108, Laurin Publishing, Pittsfield, MA.
The Photonics Dictionary, 2003 Book 4, 49th edition of The Photonics Directory, Laurin Publishing, Pittsfield, MA, www.photonics.com, pp. D-104-D106, (2003).
Pierce, Jr. et al., "Conspectus," Comprehensive Therapy 16(4):3-8, (1990).
Rosenthal, et al., "Clinical Application of Photodynamic Therapy," Ann Med. 26:405-9, (1994).
RTEC Entry Nos. WN2817000 (N-Iodosucfcinimide) and PB7000000 (Iodoform), (2001).
Rubin, D., et al., "Nanoparticulate Contrast Media, Blood-Pool and Liver-Spleen Imaging," Investigative Radiology, vol. 29, Suppl. 2, pp. s280-s283, 1994.
Schmidt-Erfurth, et al., "Photodynamic Therapy of Experimental Choroidal Melanoma Using Lipoprotein-delivered Benzoporphyrin," Opthalmology 101:89-99, (1994).
Sepaniak, M.J., et al., "High-Performance Liquid Chromatographic Studies of Coal Liquids by Laser-Based Detectors," J. of Chromatography, 211 (1981) 95-102.
Sepaniak, M.J., et al., "Laser Two-Photon Excited Molecular Fluorescence Detection for High Pressure Liquid Chromatography," Analytical Chemistry, 49 (1977) 1554-1556.
Serafini, et al., "Iodine-123-Rose Bengal: An Improved Hepatobiliary Imagine Agent," Journal of Nuclear Medicine, 1990.
She, J., Xanthenes: Fluorone Derivatives, The Journal of Organic Chemistry 57 Jul. 31, 1992, No. 16, Washington, DC, pp. 4418-4421.
Smith, E.W. and Maibach, H.I., "Percutaneous Penetration Enhancers: The Fundamentals," Percutaneous Penetration Enhancers, 1995, pp. 1-4, CRC Press, Inc., Boca Raton, Florida.
Stables, G.I., "Photodynamic Therapy, Antitumour Treatment," Cancer Treatment Reviews, vol. 21, pp. 311-323, 1995.
Streitwieser, Jr., et al., "Benzene and the Aromatic Ring," Introduction to Organic Chemistry, Second Edition, Chapter 22, pp. 652-656 (1976).
Tessman, J.W., et al., "Photochemistry of Furan-Side 8-Methoxpsoralen-Tymidine Monoadduct Inside the DNA Helix, Conversion to Diadduct and to Pyrone-Side Monoadduct," Biochemi, (1985).
Teuchner, K., et al., "Spectroscopic Properties of Potential Sensitizers for New Photodynamic Therapy Start Mechanisms via Two-Step Excited Electronic States," Photochemistry, (1995).

(56) References Cited

OTHER PUBLICATIONS

Valenzeno, Dennis P. and Pooler, John P., Cell membrane Photomodification: Relative Effectiveness of Halogenated Fluoresceins for Photohemolysis, Photochemistry and Photobio, (1982).

Wilson, "Rose Bengal Staining of Epibulbar Squamous Neoplasms," Opthalmic Surgery, vol. 7, pp. 21-23, 1976.

Wirth, M.J., et al., "Two-Photon Excited Molecular Fluorescence in Optically Dense Media," Analytical Chemistry, 49 (1977) 2054-2057.

Wirth, M.J., et al., "Very High Detectability in Two-Photon Spectroscopy," Analytical Chemistry, 62 (1990) 2103-2105.

Young, A.R., "Photocarcinogenicity of Psoralens Used in PUVA Treatment: Present Status in Mouse and Man," J. of Photochemistry and Photobiology, B: Biology, 6 (1990) 237-247.

Young, S., et al., "Gadolinium (III) Texaphyrin: A Rumor Selective Radiation Sensitizer that is Detectable by MRI," Proc. Natl. Acad. Sci., vol. 93, pp. 6610-6615, Jun. 1996.

Zajusz, A., et al., "Normobaric Oxygen as a Sensitizer in Radiotherapy for Advanced Head and Neck Cancer," Neoplasma, vol. 42, No. 3, pp. 137-140, 1996.

Johansson, S., "Analysis and Purification of Rose Bengal Sodium for Use as Reference Substance and in Pharmaceutical Preparations," Svensk Farmaceutisk, (1973).

\* cited by examiner

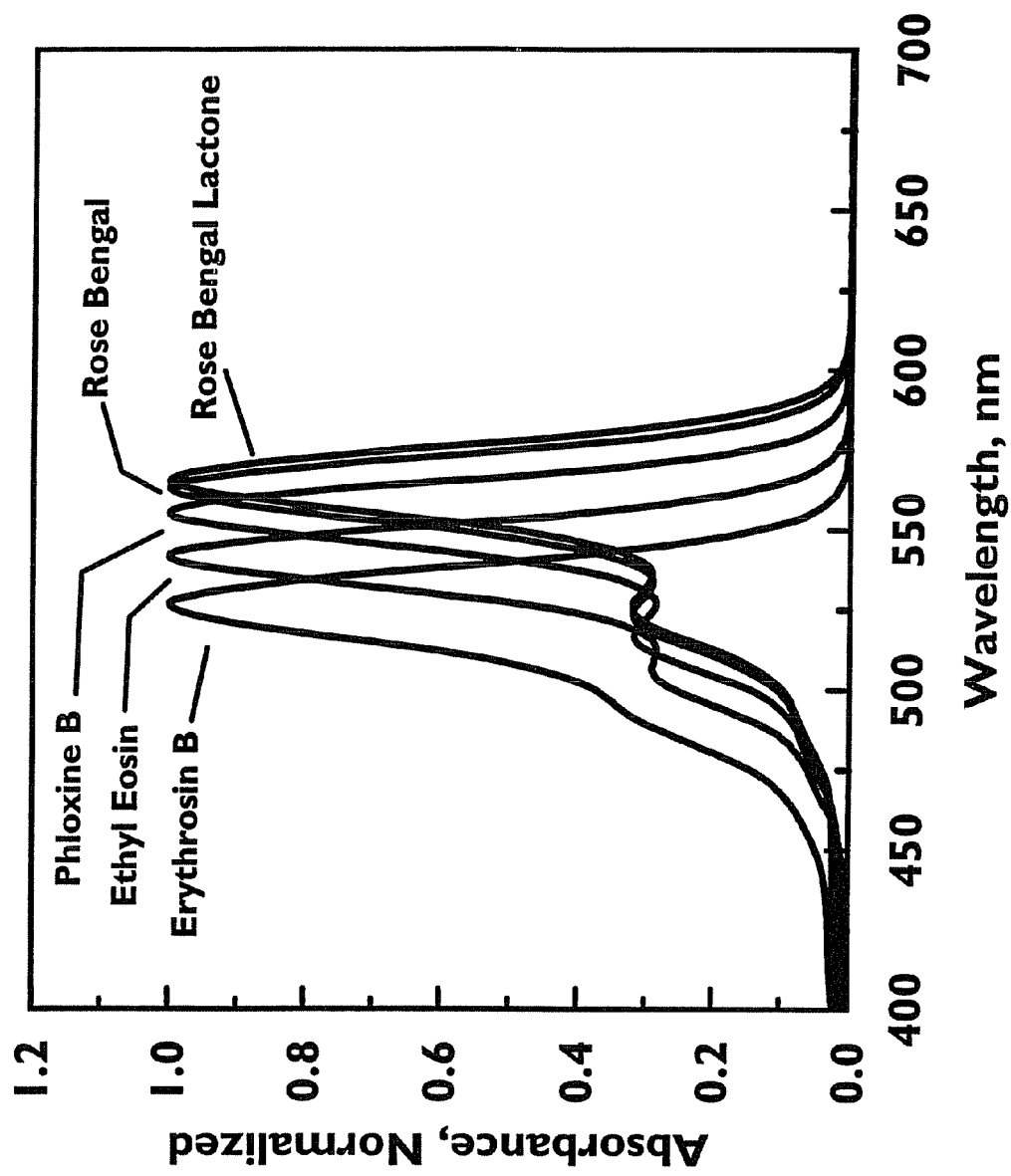

TOPICAL MEDICAMENTS AND METHODS FOR PHOTODYNAMIC TREATMENT OF DISEASE

This application is a continuation-in-part of U.S. application Ser. No. 09/635,276, filed on Aug. 9, 2000 now abandoned which claims the benefit of U.S. Provisional Application No. 60/149,015 filed Aug. 13, 1999. The '276 application is a continuation-in-part of U.S. Ser. No. 08/989,231, filed Dec. 11, 1997 (now U.S. Pat. No. 5,998,597 issued Dec. 7, 1999); U.S. Ser. No. 09/130,041, filed on Aug. 6, 1998 now abandoned; U.S. Ser. No. 09/184,388, filed on Nov. 2, 1998 (now U.S. Pat. No. 6,493,570 issued Dec. 10, 2002); and U.S. Ser. No. 09/216,787, filed on Dec. 21, 1998 (now U.S. Pat. No. 6,331,286 issued Dec. 18, 2001), which are herein incorporated by reference in their entirety.

BACKGROUND OF THE INVENTION

The present invention is related to certain photodynamic, topically-applicable medicaments and methods for treatment of human or animal tissue using photodynamic therapy (PDT).

PDT was originally developed to treat cancer and other diseases with the promise of limiting the invasiveness of the therapeutic intervention and lessening potential collateral damage to normal, non-diseased tissue. In its simplest form, PDT is the combination of a photosensitive agent with special forms of illumination to produce a therapeutic response in certain tissues, such as a tumor. The agent attains an excited, active state when it absorbs one or more photons and then is or becomes efficacious. Key elements of a successful PDT regimen include either selective application or selective uptake of a photosensitive agent into the diseased tissue and site-specific application of the activating light. PDT agents are typically applied systemically (for example, via intravenous injection or oral administration) or via localized topical application directly to diseased tissues (for example, via topical creams, ointments, or sprays). Subsequent to administration of the agent (typically 30 minutes to 72 hours later), an activating light is applied to the disease site, locally activating the agent, and destroying the diseased tissue. Light is typically applied by direct illumination of the site, or by delivery of light energy to internal locations using a fiberoptic catheter or similar device.

Most current PDT regimens are based on systemic application of porphyrin-based agents or topical or systemic application of psoralen-based agents. Examples of porphyrin-based agents include porfimer sodium (PHOTOFRIN®), hematoporphyrin-derivative (HPD), benzoporphyrin derivative (BPD), Lutex, BOPP, 5-aminolevulinic acid (ALA), and SnET$_2$. PHOTOFRIN® is one of the few agents currently licensed by the U.S. FDA. Porphyrin-based agents generally are derived from complex mixtures of natural or synthetically prepared materials, and may contain components that are lipophilic. As a possible result of this lipophilicity, porphyrin-based agents have shown a slight tendency to preferentially accumulate in some tumors and other diseased tissues. However, the targeting of such agents to diseased tissue is still unacceptably low when compared to uptake in normal tissue (i.e., at most 2-10× greater uptake in diseased tissue relative to normal tissue). The psoralens, such as 8-MOP, 5-MOP, trioxsalen, and AMT, are nucleic acid intercalators that function by impairing cellular physiology. This intercalation appears to be relatively indiscriminate in terms of tissue type, and as a result these agents also exhibit minimal specificity for diseased tissue. Thus, current agents have failed to exhibit sufficient specificity, and may exhibit additional disadvantages, including persistent systemic or localized photosensitivity, systemic or localized toxicity, and unacceptable treatment cost (due to high agent cost or excessive dosage requirements).

The inherent disadvantages of various current PDT agents and medicaments containing such agents have made acceptable PDT-based treatment of various human and animal conditions difficult or impossible. These disadvantages are particularly serious in the case of indications affecting external or internal surface or near surface tissues, where it would be desirable to have medicaments suitable for localized, selective treatment of the desired tissues. Such indications include a variety of conditions affecting the skin and related organs, the mouth and digestive tract and related organs, the urinary and reproductive tracts and related organs, the respiratory tract and related organs, as well as various other tissue surfaces, such as tissue surfaces exposed during surgery.

Therefore, it is an object of the present invention to provide new medicaments, medical uses for such medicaments based on targeted application of such medicaments and methods for treatment using such medicaments, thereby resulting in increased efficacy and safety and reduced cost of treatment.

SUMMARY OF THE PRESENT INVENTION

The present invention is directed to new photodynamic, topically-applicable medicaments and certain medical uses of such photodynamic medicaments or methods for treatment using such medicaments for treatment of human or animal tissue, wherein a primary active component of such medicaments is a halogenated xanthene, and more preferably Rose Bengal or its derivative. The halogenated xanthenes constitute a family of potent photosensitizers that become photoactivated upon illumination with visible wavelengths of light. Such medicaments can also be called pharmaceutical compositions or agents.

The inventors of the present invention have found that such medicaments are useful for treatment of a variety of conditions affecting the skin and related organs, the mouth and digestive tract and related organs, the urinary and reproductive tracts and related organs, the respiratory tract and related organs, as well as various other tissue surfaces, such as tissue surfaces exposed during surgery. These medicaments are applied in various formulations including liquid, semisolid or aerosol delivery vehicles. Photoactivation of photoactive ingredients in such medicaments produces a desirable medical response, such as destruction of microbial infection, reduction or elimination of tissue irritation, reduction or elimination of hyperproliferative tissue, reduction or elimination of cancerous or precancerous tissue, reduction or elimination of surface or subsurface lipocytes or lipid deposits, and many other similar indications.

In a preferred embodiment, such medicaments are used for treatment of a variety of conditions affecting the skin and related organs.

In another preferred embodiment, such medicaments are used for treatment of a variety of conditions affecting the mouth and digestive tract and related organs.

In another preferred embodiment, such medicaments are used for treatment of a variety of conditions affecting the urinary and reproductive tracts and related organs.

In another preferred embodiment, such medicaments are used for treatment of a variety of conditions affecting the respiratory tract and related organs.

In another preferred embodiment, such medicaments are used for treatment of a variety of conditions affecting various other internal or external tissue surfaces, such as tissue surfaces exposed during surgery.

In another preferred embodiment, such medicaments are used for treatment of a variety of conditions related to microbial or parasitic infection.

In another preferred embodiment, such medicaments are produced in various formulations including liquid, semisolid or aerosol delivery vehicles.

In a preferred embodiment, the present invention is directed to a topically-applicable medicament, the medicament consisting of: a hydrophilic vehicle containing a halogenated xanthene, wherein said halogenated xanthene is a compound selected from the group consisting of Erythrosin B, Phloxine B, Rose Bengal, and 4,5,6,7-Tetrabromoerythrosin, said halogenated xanthene at a concentration of from greater than approximately 0.0001% to less than approximately 20%; at least one at a level sufficient to achieve a medicament viscosity in the range of approximately 10-1000 cps; and an electrolyte selected from the group consisting of sodium, potassium, calcium and magnesium chlorides, phosphates, and nitrates, wherein the electrolyte is at a concentration of approximately 0.1-2%, or wherein the electrolyte is at a level sufficient to provide an osmolality of the medicament of greater than approximately 100 mOsm/kg.

BRIEF DESCRIPTION OF THE DRAWINGS

In describing the preferred embodiments, reference is made to the accompanying drawings wherein:

FIG. 2 shows example absorbance spectra of several halogenated xanthenes.

DETAILED DESCRIPTION OF THE PRESENTLY PREFERRED EMBODIMENTS

The present invention is directed to new photodynamic, topically-applicable medicaments and certain medical uses of such photodynamic medicaments or methods for treatment using such medicaments for treatment of human or animal tissue, wherein a primary active component of such medicaments is a halogenated xanthene. Such halogenated xanthenes discussed infra are capable of exhibiting a desirable photodynamic effect when applied to or otherwise delivered to certain human or animal tissues, and undergo photodynamic activation in such tissues upon illumination with visible, and in particular green, light. These desirable effects include reduction or elimination of disease or other undesirable conditions, including eradication of cancerous or precancerous tumors and infectious agents, and are applicable to a variety of conditions affecting the skin and related organs, the mouth and digestive tract and related organs, the urinary and reproductive tracts and related organs, the respiratory tract and related organs, and various other internal or external tissue surfaces, such as tissue surfaces exposed during surgery.

In a preferred embodiment, such medicaments are produced in various formulations including liquid, semisolid or aerosol delivery vehicles.

1. Properties of the Preferred Photoactive Components and Medicament Formulations.

Figure 1A:
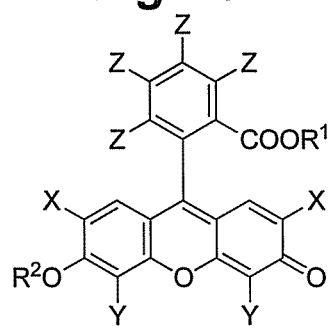
FIG. 1(a) shows the generalized chemical structure of the halogenated xanthenes.

The applicants have discovered that a certain class of photoactive agents are broadly applicable for producing topically-applicable medicaments for treatment of certain human and animal tissues. These photoactive agents are referred to as halogenated xanthenes and are illustrated in FIG. 1a, where the symbols X, Y, and Z represent various elements present at the designated positions, and the symbols $R^1$ and $R^2$ represent various functionalities present at the designated positions.

Selected chemical and physical properties (such as the chemical constituents at positions X, Y, and Z and the functionalities $R^1$ and $R^2$, along with molecular weight and photochemical characteristics) of representative halogenated xanthenes are summarized in attached Table 1. The general properties of this class of agents are discussed in further detail in U.S. Ser. No. 09/130,041, filed on Aug. 6, 1998, U.S. Ser. No. 09/184,388, filed on Nov. 2, 1998, and U.S. Ser. No. 09/216,787, filed on Dec. 21, 1998, which are herein incorporated by reference in their entirety. In general, the halogenated xanthenes are characterized by a low dark cytotoxicity (toxicity to cells or tissues in the absence of photoactivation), high light cytotoxicity (toxicity to cells or tissues upon photoactivation) and chemical and photochemical properties that are substantially unaffected by the local chemical environment or the attachment of functional derivatives at positions $R^1$ and $R^2$. This makes such chemical agents, and in particular medicaments formulated from such agents, excellent PDT agents for the treatment of human and animal tissues.

It is thus a preferred embodiment of the present invention that a topically-applicable medicament be produced that contains, as an active ingredient at a concentration of from greater than approximately 0.0001% to less than approximately 20%, at least one halogenated xanthene. It is further preferred that the concentration of the at least one halogenated xanthene be in the range of from approximately 0.0001% to 0.01%, and more preferably from approximately 0.0005% to 0.005%. It is even more preferred that this concentration is approximately 0.001%. These preferred concentrations may be weight to volume (w/v) or weight to weight (w/w). The inventors have found that the lower concentration ranges are especially preferred because at concentrations above approximately 0.01%, the medicament may exhibit excessive optical density, rendering the absorbance of activating light by superficial levels of tissue sufficiently high to interfere with delivery of activating light to underlying tissue.

Figure 1B:
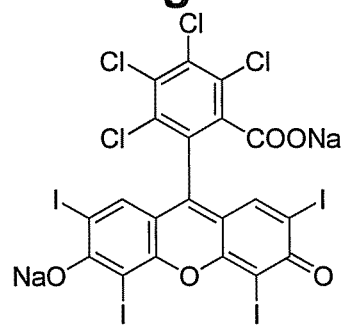
FIG. 1(b) shows the chemical structure of Rose Bengal.

It is further preferred that this medicament include the halogenated xanthene Rose Bengal (4,5,6,7-tetrachloro-2',4', 5',7'-tetraiodofluorescein, illustrated in FIG. 1b).

Other example halogenated xanthenes that can be used in the present invention include, but are not limited to, one or more of: Fluorescein; 4',5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal; 4,5,6,7-Tetrabromoerythrosin; Mono-, Di-, or Tribromoerythrosin; Mono-, Di-, or Trichloroerythrosin; Mono-, Di-, or Tricfluoroerythrosin; 2',7'-Dichloro-4,5,6,7-Tetrafluorofluorescein; 2',4,5,6,7,7'-Hexafluorofluorescein; and 4,5,6,7-Tetrafluorofluorescein.

Further, as evidenced by the data shown in Table 1 and in FIG. 2, it is clear that the halogenated xanthenes share common spectroscopic properties, including a high single-photon cross-section extending from approximately 500 nm to 600 nm. These properties are substantially invariant regardless of state of derivatization (for example, at positions $R^1$ and $R^2$) or of chemical or biological environment. This feature facilitates photoactivation with commonly available visible light sources, such as cw or pulsed lasers or lamps, operating in the band from approximately 500 nm to 600 nm, and circumvents the need to substantively change sources if the specific photoactive component of the medicament is varied or modified, as disclosed herein. Furthermore, the inventors of the present invention have shown that the halogenated xanthenes are capable of being activated using non-linear, multi-photon excitation under certain conditions when using light in the near infrared band from approximately 700 nm to 1200 nm (using methods, such as for example, those taught in U.S. Ser. No. 08/989,231, filed Dec. 11, 1997 and U.S. Ser. No. 09/096,832 filed Jun. 12, 1998, which are incorporated herein by reference). Such excitation methods provide additional utility in activation of medicaments formulated from such agents, such as for example when it is desirable to increase the depth of photoactivation to positions substantially below an exposed tissue surface.

As an example of these desirable chemical, biochemical, and physical properties, the inventors have found that the prototypical halogenated xanthene, Rose Bengal, will accumulate preferentially in (i.e. target) some tumors and other diseased tissues and pathogens, has negligible dark cytotoxicity, high light cytotoxicity upon illumination with visible light, relatively low cost, and the ability to clear rapidly from the body.

Moreover, the inventors have discovered that the facility with which the halogenated xanthenes target specific tissues or other sites can be further optimized by attachment of specific functional derivatives at positions $R^1$ and $R^2$, so as to change the chemical partitioning or biological activity of the agent. For example, attachment of one targeting moiety or more at positions $R^1$ or $R^2$ can be used to improve targeting to specific tissues, such as cancerous tumor tissues or sites of localized infection. An example of this is esterification at position $R^1$ with a short aliphatic alcohol, such as n-hexanol, to produce a derivatized agent exhibiting enhanced partitioning into lipid-rich tumor tissues.

It is thus a further preferred embodiment that at least one of the at least one halogenated xanthene active ingredients includes at least one targeting moiety selected from a group that includes DNA, RNA, amino acids, proteins, antibodies, ligands, haptens, carbohydrate receptors or complexing agents, lipid receptors or complexing agents, protein receptors or complexing agents, chelators, encapsulating vehicles, short- or long-chain aliphatic or aromatic hydrocarbons, including those containing aldehydes, ketones, alcohols, esters, amides, amines, nitriles, azides, or other hydrophilic or hydrophobic moieties. A further example of this embodiment is derivatization of Rose Bengal with a lipid (at position $R^1$, via esterification), so as to increase the lipophilicity of Rose Bengal, and thereby modify its targeting properties in a patient.

As an alternative, $R^1$ and $R^2$ may preferably be independently selected from hydrogen ($H^+$), sodium ($Na^+$), potassium ($K^+$), calcium ($Ca^+$) and ammonium ($NH_4^+$) ions. Hence, $R^1$ and $R^2$ can both be the same one of these ions, or $R^1$ and $R^2$ can be different ones of these ions.

Because the halogenated xanthenes and their derivatives are, in general, solids in their pure form, it is preferred that, for proper delivery to desired tissues, such agents be formulated in appropriate delivery vehicles. Approaches to such formulation will be generally known to those of ordinary skill in the art. Specifically, such formulations are preferred so as to facilitate agent contact with, and delivery to, desired tissues to be treated.

It is thus a further preferred embodiment of the present invention that at least one halogenated xanthene or halogenated xanthene derivative be formulated as a medicament in a topically-applicable form, such as in a liquid, semisolid, solid or aerosol delivery vehicle, including aqueous, non-aqueous or nanoparticulate suspensions, solutions, creams, ointments, gels, syrups, suppositories or micro-droplet sprays. The at least one halogenated xanthene or halogenated xanthene derivative may be dissolved or suspended in such delivery vehicle, wherein this vehicle may, in addition to the at least one halogenated xanthene or halogenated xanthene derivative, include various builders, stabilizers, emulsifiers or dispersants, preservatives, buffers, electrolytes, and tissue penetrating or softening agents. Such components of the delivery vehicle may be present as the primary component (by weight or volume) of the medicament, or as a minor component that serves in an adjuvant role in agent delivery.

For example, appropriate builders include cellulose and cellulose derivatives, such as starch, and alginates. Additional examples include various carboxymethylcelluloses and derivatives thereof, especially those of medium to high viscosity, such as USP carboxymethylcellulose. The inventors have found that use of one or more builders at a level sufficient to achieve a medicament viscosity in the range of approximately 10-1000 cps, and more preferable in the range of approximately 50-500 cps, and even more preferably in the range of approximately 75-250 cps, is advantageous for effective application of the medicament to tissue and delivery of the active halogenated xanthene component to tissue.

Examples of appropriate stabilizers, emulsifiers or dispersants include liposomes, nanoparticulates and nanodispersions, microparticulates and microdispersions, as well as various lipids, detergents and other surfactants.

Examples of appropriate preservatives include benzalkonium chloride, thimerosal, and urea. Additional examples of appropriate preservatives include chlorhexidine, imidurea, methyl-paraben and propyl-paraben. The inventors have found that it is generally preferable to avoid use of preservatives, many of which may deleteriously interfere with the medicament or formulation thereof, or may complex with or otherwise interact with or interfere with delivery of the active halogenated xanthene component therein. To the extent that a preservative is to be used, the inventors have found that imidurea is preferred as it does not appear to interact with the halogenated xanthenes, either in the medicament or upon administration, nor to deleteriously affect the medicament formulation.

Examples of appropriate buffers include monobasic or dibasic phosphate salts, citrate salts, bicarbonate salts, and ethanolamine.

Examples of appropriate electrolytes include sodium, potassium, calcium and magnesium chlorides, phosphates, and nitrates. Sodium, such as in the form of sodium chloride, is a preferred embodiment as the electrolyte due to its inherent physiologic compatibility. The inventors have found that it is preferable that such electrolyte be present in the medicament at a concentration of approximately 0.1-2%, and more preferably at a concentration of approximately 0.5-1.5%, and even more preferably at a concentration of approximately 0.8-1.2%, and most preferably at a concentration of approximately 0.9%. Electrolytes at such levels increase the osmolality of the medicament, which the inventors have found to increase the preference for partitioning of the halogenated xanthene component into tissue. Thus, as an alternative to the previously specified range of electrolyte concentrations, osmolality may be used to characterize, in part, the electrolyte level of the preferred medicament. It is preferred that the osmolality of the medicament be greater than approximately 100 mOsm/kg, and more preferably that it be greater than approximately 250 mOsm/kg, and most preferably that it be approximately 300-500 mOsm/kg.

Examples of appropriate tissue penetrating, softening or solvating agents and adjuvants include:

various sulfoxides, such as DMSO and decylmethylsulfoxide;

various aliphatic and fatty alcohols, such as ethanol, propanol, hexanol, octanol, benzyl alcohol, decyl alcohol, lauryl alcohol, and stearyl alcohol;

various linear and branched, saturated and unsaturated fatty acids, such as lauric acid, caproic acid, capric acid, acid, myristic acid, stearic acid, oleic acid, isovaleric acid, neopentanoic acid, trimethyl hexanoic acid, neodecanoic acid and isostearic acid;

various aliphatic and alkyl fatty acid esters, including isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate and ethyl oleate;

various polyols, such as propylene glycol, polyethylene glycol, ethylene glycol, diethylene glycol, triethylene glycol, diproplyene glycol, glycerol, propanediol, butanediol, pentanediol and hexanetriol;

various amides, such as urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methyoxycarbonyl-2-pyrrolidone, 1-methyl-4-methyoxycarbonyl-2-pyrrolidone, 1-lauryl-4-methyoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives, such as fatty acid esters of N-(2-hyroxyethyl)-2-pyrrolidone; cyclic amides, such as 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethydrodecyl)azacycloheptan-2-one, 1-geranylazacyclohexane-2-one, 1-geranylazacyclopentan-2,5-dione, 1-farnesylazacyclopentan-2-one; hexamethylenelauramide and its derivatives; and diethanolamine and triethanolamine;

various surfactants, such as anionic surfactants, including sodium laurate and sodium lauryl sulfate; cationic surfactants, including cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; nonionic surfactants, such as Polaxamer (231, 182, 184), Brij (30, 93, 96, 99), Span (20, 40, 60, 80, 85), Tween (20, 40, 60, 80), Myrj (45, 51, 52), Miglyol 840; various bile salts, such as sodium cholate, sodium salts of taurocholic, glycholic, desoxycholic acids; lecithin; various terpenes, including hydrocarbons, such as D-limonene, α-pinene, β-carene; various terpene alcohols, including α-Terpineol, terpinen-4-ol, carvol; various terpene ketones, including carvone, pulegone, piperitone, menthone; various terpene oxides, including cyclohexane oxide, limonene oxide, α-pinene oxide, cyclopentene oxide, 1,8-cineole; various terpene oils, including ylang ylang, anise, chenopodium, eucalyptus;

various alkanones, such as N-heptane, N-octane, N-nonane, N-decane, N-undecane, N-dodecane, N-tridecane, N-tetradecane, N-hexadecane;

various organic acids, such as salicylic acid and salicylites (including their methyl, ethyl, and propyl glycol derivatives), citric and succinic acid.

In addition to the examples cited here, other topically-applicable formulations familiar to those of ordinary skill in the art, including various simple or complex combinations of vehicles and adjuvants, will be useful for improving delivery of the photoactive component of the medicament to target tissues. Background on such vehicles and adjuvants may be found, for example, in: E. W. Smith and H. I. Maibach, "Percutaneous Penetration Enhancers: The Fundamentals"; S. C. Chattaraj and R. B. Walker, "Penetration Enhancer Classification"; and B. J. Aungst, "Fatty Acids as Skin Permeation Enhancers"; in E. W. Smith and H. I. Maibach (eds), *Percutaneous Penetration Enhancers*, CRC Press, Boca Raton, 1995. These references are incorporated herein by reference in their entirety.

Further, appropriate topically-applicable medicament formulations can, for example, incorporate various complex delivery vehicles, including various commercial vehicles, such as those available from Paddock Laboratories, including Dermabase®, Hydrocream, Aquabase, Liquaderm-A, Liqua-Gel, Ora-Plus®, Ora-Sweet® and Ora-Sweet SF, Suspendol-S, Fattibase and Polybase, as well as various proprietary vehicles, such as propylene glycol with one or more adjuvant delivery agent, so as to enhance delivery of the at least one halogenated xanthene or halogenated xanthene derivative to desired tissues to be treated. A comparison of the delivery properties for several example formulations is provided in Table 2, showing that both the quantity of active ingredient delivered to various tissues and the depth of such delivery beyond the application point can be substantially controlled by medicament formulation.

The inventors have found that delivery of the halogenated xanthene component of these medicaments is most favorable when the medicament has a pH close to physiologic pH (i.e., approximately 7), and especially when the pH is greater than about 4, thereby assuring that the halogenated xanthenes remain in dibasic form in the medicament. Thus, in a preferred embodiment, the pH of the medicament is in the range from approximately 4-10, and more preferably in the range from approximately 5-9, and most preferably in the range from approximately 6-8.

Finally, the inventors have found that a hydrophilic vehicle is preferred for the medicament to maximize preference for partitioning of the halogenated xanthene component into tissue. Accordingly, in a preferred embodiment, the vehicle contains a minimum of non-hydrophilic components that might interfere with such partitioning.

Accordingly, the inventors have found that a preferred formulation of the topically-applicable medicaments contain, in a hydrophilic vehicle:

(1) an active halogenated xanthene ingredient at a concentration of from greater than approximately 0.0001% to less than approximately 20% of at least one halogenated xanthene;

(2) at least one builder (i.e. one or more builder) at a level sufficient to achieve a medicament viscosity in the range of approximately 10-1000 cps; and (3) an electrolyte selected from sodium, potassium, calcium and magnesium chlorides, phosphates, and nitrates, wherein the electrolyte is present at a concentration of approximately 0.1-2%, or alternately at a level sufficient to provide an osmolality of greater than approximately 100 mOsm/kg.

In a further preferred embodiment, the halogenated xanthene is at a concentration in the range of from approximately 0.0001% to 0.01%, and even more preferably from approximately 0.0005% to 0.005%, and most preferably that this concentration is approximately 0.001%.

In a further preferred embodiment, the at least one builder is selected from the group including cellulose and cellulose derivatives, such as starch, alginates, and various carboxymethylcelluloses and derivatives thereof, especially those of medium to high viscosity, such as USP carboxymethylcellulose.

In a further preferred embodiment, the at least one builder is in the range of approximately 50-500 cps, and even more preferably in the range of approximately 75-250 cps.

In a further preferred embodiment, the electrolyte is preferably sodium chloride.

In a further preferred embodiment, the electrolyte is at a concentration of approximately 0.5-1.5%, and even more preferably at a concentration of approximately 0.8-1.2%, and most preferably at a concentration of approximately 0.9%.

In a further preferred embodiment, the electrolyte is present at a level sufficient to provide an osmolality of the medicament of greater than 250 mOsm/kg, and most preferably approximately 300-500 mOsm/kg.

It is further preferred that the hydrophilic vehicle consist of water.

It is also further preferred that the medicament have a pH close to physiologic pH (i.e., approximately 7), and especially a pH of greater than about 4, and preferably in the range from approximately 4-10, and more preferably in the range from approximately 5-9, and most preferably in the range from approximately 6-8.

It is also further preferred that the at least one halogenated xanthene consist of Rose Bengal or a functional derivative of Rose Bengal, including those containing hydrogen ($H^+$), sodium ($Na^+$), potassium ($K^+$), calcium ($Ca^+$) or ammonium ($NH_4^+$) ions at positions $R^1$ and $R^2$.

It is most preferred that the topically-applicable medicament contain only, in a hydrophilic vehicle, at least one halogenated xanthene, a builder, and an electrolyte, wherein such medicament has a pH close to physiologic pH.

It is further preferred that the topically-applicable medicament contain a microbial load of no more than 10 colony forming units (cfu) per 1 mL (i.e., NMT 10 cfu/mL) to conform with UPS <61> microbial limits specifications.

The inventors have found that the aforementioned medicaments are suitable for activation using applied light, such as that produced by lasers, light emitting diodes and lamps, including fluorescent lamps, and under some circumstances may be successfully activated upon exposure to ambient light, such as room light or daylight. Specifically, the inventors have found that such activation may occur, following application of the medicament to tissue, upon exposure of such tissue to light at moderate intensities, such as 25 mW/cm² or less, and at moderate doses, such as 25 J/cm² or less, and frequently at intensities of 10 mW/cm² or less and at doses of 10 J/cm² or less. The inventors have found that compatibility with the latter combination of intensity and dose makes these medicaments particularly suitable for activation using ambient light. Such activation using ambient light is particularly relevant to the treatment of conditions affecting the skin and related organs, and especially large areas of skin an related organs, as described in the following section.

The inventors have further found that the preferred topically-applicable medicaments may be photodegraded upon prolonged exposure to ambient light. It is thus further preferred that such medicaments be packaged in a light protective primary container, such as an opaque container, or that the primary container be enclosed in a light-resistant or light-proof outer secondary container, such as an overpack box or foil pouch, to minimize or prevent exposure to ambient light prior to use. The inventors have further found that standard amber light-resistant containers do not adequately prevent exposure of the medicaments to visible light in the photoactive 500-600 nm band, and so such containers are inadequate for protection of the medicaments and should be avoided.

2. Methods and Medical Use of the Subject Medicament for Treatment of Conditions Affecting the Skin and Related Organs.

The applicants have discovered that the medicaments disclosed herein are broadly applicable to improved treatment of various conditions affecting the skin and related organs of humans and animals. The medicament can be applied directly to, or substantially proximal to, tissues to be treated, including those of the skin, nails, scalp and oral cavity. Example indications include treatment for: Psoriasis and Pustular Psoriasis; Reiter's Syndrome; Skin Ulcers, including Stasis Dermatitis, Stasis Ulcers, Ischemic Ulcers, Sickle Cell Leg Ulcers, Diabetic Ulcers, Inflammatory Ulcers; Eczematous Disease and Eczematous Reaction; various Ichthyoses; Atopic Dermatitis; Superficial Wrinkles; Near Surface Fat Reduction; Benign and Malignant Proliferative Disorders, such as Benign Epithelial Tumors and Hamartomas; Premalignant and Malignant Epithelial Tumors, including Actinic Keratoses, Basal Cell Carcinoma, Squamous Cell Carcinoma, and Keratoacanthoma; Benign and Malignant Adnexal Tumors; Tumors of Pigment-Producing Cells, including Malignant Melanoma, Solar Lentigines, Nevi, and Café-au-lait; Sarcomas; Lymphomas; Vascular Disorders; such as Hemangiomas and Port Wine Stain; Microbial Infection, such as Bacterial, Fungal, Yeast, Parasitic or Other Infections; Warts; and Acne.

In an example of a preferred embodiment of this method of treatment or medical use, applicants have found that application of a cream or solution containing Rose Bengal at a concentration of approximately 0.1% W/V to persistent leg ulcers, followed, after a latency period of 0-72 hours, and more preferably 0-1 hour, by illumination with approximately 10 to 200 J/cm² of continuous or pulsed green light in the 500-600 nm band, leads to substantial or complete healing of such persistent leg ulcers, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the skin and related organs of humans and animals.

3. Methods and Medical Use of the Subject Medicament for Treatment of Conditions Affecting the Mouth and Digestive Tract and Related Organs The applicants have discovered that the medicaments disclosed herein are broadly applicable to improved treatment of various conditions affecting the mouth and digestive tract and related organs of humans and animals. The medicament can be applied directly to, or substantially proximal to, tissues to be treated, including those of the mouth, gums, tongue, larynx, pharynx, esophagus, stomach, intestines and colon. Example indications include treatment for: Benign Esophageal Lesions, Barretts Esophagus and other Esophageal Hyperplasia and Dysplasia, and Esophageal Cancer, including Squamous Cell Carcinoma, Adenocarcinoma, Carsinosarcoma, Pseudosarcoma, and Sarcoma; Gastric Ulcers, Leiomyomas, Polyps, Neoplasms, Lymphoma and Pseudolymphoma, Adenocarcinoma, Primary Lymphoma, Leiomyosarcoma; Oral and Oropharynx Cancer and Premalignancies, Ulcers and Inflammatory Lesions, including Squamous Cell Carcinoma, Lymphoma, Actinic Cheilitis, Nicotine Stomatitis, Leukoplakia, Erythroplakia; Gum and Other Periodontal Disease, including Gingivitis; Laryngeal Hyperplasia, Dysplasia and Neoplasms; Colorectal Cancer and Polyps.

In an example of a preferred embodiment of this method of treatment or medical use, applicants have found that application of a solution containing Rose Bengal at a concentration of approximately 1% W/V in saline to esophageal tissue, followed, after a latency period of 0-72 hours, and more preferably 0-1 hour, by illumination with approximately 10 to 200 $J/cm^2$ of continuous or pulsed green light in the 500-600 nm band, leads to substantial or complete eradication of diseased tissues, such as those present in Barretts esophagus, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the mouth and digestive tract and related organs of humans and animals.

4. Methods and Medical Use of the Subject Medicament for Treatment of Conditions Affecting the Urinary and Reproductive Tracts and Related Organs.

The applicants have discovered that the medicaments disclosed herein are broadly applicable to improved treatment of various conditions affecting the urinary and reproductive tracts and related organs of humans and animals. The medicament can be applied directly to, or substantially proximal to, tissues to be treated, including those of the urethra, bladder, ureter, kidneys, vulva, vagina, cervix, fallopian tubes, ovaries, penis, testes, vas deferens, prostate, and epididymis. Example indications include treatment for: Urinary Tract Disease, including Cancerous and Pre-Cancerous Hyperplasia, Dysplasia and Neoplasms, Tumors and other Growths, Inflammation, and Infection of the Bladder, Ureter, Urethra, and Kidney; Cancerous and Pre-Cancerous Hyperplasia, Dysplasia and Neoplasms, Tumors and other Growths, Inflammation, and Infection of the Cervix, Endometrium, Myometrium, Ovaries, Fallopian Tubes, Uterus, Vulva, and Vagina; Cancerous and Pre-Cancerous Hyperplasia, Dysplasia and Neoplasms, Tumors and other Growths, Inflammation, and Infection of the Prostate and Testes; Reproductive Tract Infections, including Tinea Cruris, Candidiasis, Condylomata Acuminata, Molluscum Contagiosum, Genital Herpes Simplex Infection, Lymphogranuloma Venereum, Chancroid, Granuloma Inguinale, Erythrasma; Psoriasis; and Lichen Planus and Lichen Sclerosus.

In an example of a preferred embodiment of this method of treatment or medical use, applicants have found that application of a solution containing Rose Bengal at a concentration of approximately 1% W/V to tissue, followed, after a latency period of 0-72 hours, and more preferably 0-1 hour, by illumination with approximately 10 to 200 $J/cm^2$ of continuous or pulsed green light in the 500-600 nm band, leads to substantial or complete eradication of diseased tissues, such as those present in bladder tumors, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the urinary and reproductive tracts and related organs of humans and animals.

5. Methods and Medical Use of the Subject Medicament for Treatment of Conditions Affecting the Respiratory Tract and Related Organs.

The applicants have discovered that the medicaments disclosed herein are broadly applicable to improved treatment of various conditions affecting the respiratory tract and related organs of humans and animals. The medicament can be applied directly to, or substantially proximal to, tissues to be treated. Example indications include treatment for: Hyperplasia, Dysplasia and Neoplasia, Cancer, Inflammation and Infection of the Nasal Cavity, Paranasal Sinuses, Tear Ducts, Eustachian Tubes, Nasopharynx, Hypopharynx, Larynx, Trachea, Bronchi, Lung and Alveoli.

In an example of a preferred embodiment of this method of treatment or medical use, applicants have found that application of a solution containing Rose Bengal at a concentration of approximately 1% W/V to tissue, followed, after a latency period of 0-72 hours, and more preferably 0-1 hour, by illumination with approximately 10 to 200 $J/cm^2$ of continuous or pulsed green light in the 500-600 nm band, leads to substantial or complete eradication of diseased tissues, such as those present in tracheal tumors, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the respiratory tracts and related organs of humans and animals.

6. Methods and Medical Use of the Subject Medicament for Treatment of Conditions Affecting Various Other Internal or External Tissue Surfaces Such as Tissue Surfaces Exposed During Surgery.

The applicants have discovered that the medicaments disclosed herein are broadly applicable to improved treatment of various conditions affecting various other internal or external tissue surfaces of humans or animals, such as tissue surfaces exposed during surgery, including endoscopic surgery or other endoscopic procedures. The medicament can be applied directly to, or substantially proximal to, tissues to be treated. Example indications include treatment for: Joint Inflammation, such as that of Arthritis; Resected Tumor Beds of Intracranial and other Head and Neck, Thoracic, or Abdominal Tumors; Cardiac and Pericardial Tissues and Circulatory Tissues, including Arteries and Veins, including Plaques and Infections of such tissues, such as Bacterial Endocarditis; Metastatic Tumors, such as Metastases of Breast Tumors to the Skin; and various other substantially similar indications.

In an example of a preferred embodiment of this method of treatment or medical use, applicants have found that application of an aqueous solution containing Rose Bengal at a concentration of approximately 10% W/V micromolar to breast adenocarcinoma and sarcoid tissues, followed, after a latency period of 0-72 hours, and more preferably 0-1 hour, by illumination with approximately 10 to 200 $J/cm^2$ of continuous or pulsed green light in the 500-600 nm band, leads to substantial or complete eradication of such tissues, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of various other internal or external tissue surfaces of humans or animals, such as tissue surfaces exposed during surgery.

7. Methods and Medical Use of the Subject Medicament for Treatment of Conditions Related to Microbial or Parasitic Infection.

The applicants have discovered that the medicaments disclosed herein are broadly applicable to improved treatment of various conditions related to microbial or parasitic infection of humans or animals, including those infections resistant to conventional treatments. The medicament can be applied directly to, or substantially proximal to, tissues to be treated. Example indications include treatment for: Bacterial and Antibiotic Resistant Bacterial Infection, including those caused by Gram Positives and Gram Negatives, *Streptomycetes, Actinomycetes, Staphylococci, Streptococci, Pseudomonas, Escherichia coli, Mycobacteria* and others; Infection caused by Filamentous Fungi and Non-filamentous Fungi like *Cryptosporidium, Histoplasma, Aspergillus, Blastomyces, Candida* and others; Parasitic Infection caused by Amoeba (including for use in lysing and killing amoeba in amoebic cysts), *Trichinella, Dirodfilaria* (Heart worm in dogs) and others.

In an example of a preferred embodiment of this method of treatment or medical use, applicants have found that application of an aqueous solution containing Rose Bengal at a concentration of approximately 1 to 10 micromolar or greater to antibiotic resistant *Staphylococcus aureus, Escherichia coli*, various other gram positive and gram negative bacteria, and various yeasts, followed, after a latency period of 0-72 hours, and more preferably 0-1 hour, by illumination with approximately 10 to 200 J/cm$^2$ of continuous or pulsed green light in the 500-600 nm band, leads to substantial or complete eradication of such microbes, with little or no side effects in surrounding tissue. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of various other conditions related to microbial or parasitic infection of humans or animals.

8. Additional Properties of the Topically-Applicable Medicaments

Details defining parameters such as composition of the topically-applicable medicament, methods of administration, and directions for usage should be consistent with relevant U.S. federal and international regulations (such as those promulgated by the International Conference on Harmonization, ICH) covering pharmaceutical products. Such regulations, including those promulgated by the U.S. Food and Drug Administration ("FDA") in Title 21 of the Code of Federal Regulations (CFR), strictly regulate medical products within the jurisdictional territories of the respective regulatory agencies. Among other parameters, such regulations define specific features of any such medical product, and in particular certain aspects of the manufacturing and labeling of such medical products. Accordingly, such features are an inherent element of the topically-applicable medicaments described herein. Particularly relevant features relate to identification of the medicament and directions for its usage (i.e., product labeling).

For instance, the FDA has detailed labeling requirements concerning the recital of ingredients and directions for use for any medical product sold in interstate commerce. These requirements are enumerated in Title 21, Section 201, Subpart A ("General Labeling Provisions") of the CFR. For example, 21 CFR §201.5 ("Drugs; adequate directions for use") requires detailed labeling concerning intended use and dosage:

"Adequate directions for use means directions under which the layman can use a drug safely and for the purposes for which it is intended. (Section 201.128 defines "intended use.") Directions for use may be inadequate because, among other reasons, of omission, in whole or in part, or incorrect specification of:
(a) Statements of all conditions, purposes, or uses for which such drug is intended, including conditions, purposes, or uses for which it is prescribed, recommended, or suggested in its oral, written, printed, or graphic advertising, and conditions, purposes, or uses for which the drug is commonly used; except that such statements shall not refer to conditions, uses, or purposes for which the drug can be safely used only under the supervision of a practitioner licensed by law and for which it is advertised solely to such practitioner.
(b) Quantity of dose, including usual quantities for each of the uses for which it is intended and usual quantities for persons of different ages and different physical conditions.
(c) Frequency of administration or application.
(d) Duration of administration or application.
(e) Time of administration or application (in relation to time of meals, time of onset of symptoms, or other time factors).
(f) Route or method of administration or application.
(g) Preparation for use, i.e., shaking, dilution, adjustment of temperature, or, other manipulation or process."

Thus, the FDA mandates labeling that makes intended use clear even to the layman. Moreover, the FDA also strictly regulates the quantitative, definitive identification of drug ingredients; 21 CFR §201.10 ("Drugs; statement of ingredients") states:

"(a) The ingredient information . . . shall appear together, without any intervening written, printed, or graphic matter, . . . .
(b) The term ingredient applies to any substance in the drug, whether added to the formulation as a single substance or in admixture with other substances . . . ."

Accordingly, at an absolute minimum, all medicaments and pharmaceutical compositions must bear detailed marking (i.e., labeling) describing use and composition.

Subpart B ("Labeling Requirements from Prescription Drugs") of Section 201 codifies unique features required of all prescription medicaments and pharmaceutical preparations, as illustrated by the following passages:

"21 CFR §201.56 (General requirements on content and format of labeling for human prescription drugs)
"Prescription drug labeling . . . shall contain the information in the format required by §201.57 and shall meet the following general requirements:
(d)(1) The labeling shall contain specific information . . . under the following section headings and in the following order:

Description
Clinical Pharmacology.
Indications and Usage.
Contraindications.
Warnings.
Precautions.
Adverse Reactions.
Drug Abuse and Dependence.
Overdosage.
Dosage and Administration.
How Supplied."

Section 201.57 ("Specific requirements on content and format of labeling for human prescription drugs") expands on these enumerated requirements, stating, for example, that the labeling of a prescription product shall contain the following description:

"(i) The proprietary name and the established name, if any . . . of the drug;
(ii) The type of dosage form and the route of administration to which the labeling applies;
(iii) The same qualitative and/or quantitative ingredient information as required under §201.100(b) for labels;
(iv) If the product is sterile, a statement of that fact;
(v) The pharmacological or therapeutic class of the drug;
(vi) The chemical name and structural formula of the drug;
(vii) If the product is radioactive, a statement of the important nuclear physical characteristics, such as the principal radiation emission data, external radiation, and physical decay characteristics.
(2) If appropriate, other important chemical or physical information, such as physical constants, or pH, shall be stated."

Subsequent passages in this section define labeling for indications and usage, for dosage and administration, and for the other parameters identified in section 201.56, supra.

Subpart C ("Labeling Requirements for Over-the-Counter Drugs", §§201.61-201.66) codifies similar requirements for non-prescription medicaments and pharmaceutical preparations, while Subpart D ("Exemptions from Adequate Directions for Use", §§201.100-201.129) defines similar requirements for experimental products as well as bulk packages intended for distribution through pharmacies and similar channels.

Finally, concerning intended use for a drug, section 201.128 ("Meaning of 'intended uses'") states:

"The words intended uses or words of similar import . . . refer to the objective intent of the persons legally responsible for the labeling of drugs. The intent is determined by such persons' expressions or may be shown by the circumstances surrounding the distribution of the article. This objective intent may, for example, be shown by labeling claims, advertising matter, or oral or written statements by such persons or their representatives."

Thus, intended use must be conveyed on the label of all pharmaceutical products, in all product advertising, and in any other statements about the product.

These federal regulations make it clear that any drug product, such as the presently claimed medicament, is, within all jurisdictions of the U.S., strictly regulated by the FDA, and must include detailed labeling concerning composition and intended use.

The manufacturer is legally responsible for assuring compliance with these FDA requirements.

As such, these requirements assure that the commercial channels for any medicament such as those of the present application are clearly distinct from other non-pharmaceutical products, including those that might include Rose Bengal or another halogenated xanthene. Furthermore, the topically-applicable medicaments of the present application are clearly distinct from other pharmaceutical products that include Rose Bengal or another halogenated xanthene, provided that the other pharmaceutical products have a different formulation (dosage form), route of administration or indication (intended use) from that of topically-applicable medicaments of the present application.

This distinction is illustrated by experience of the inventors, who are undertaking development of two products, (1) a topical photodynamic medicament for treatment of psoriasis and (2) an injectable chemotherapeutic medicament for treatment of cancer, both of which contain Rose Bengal as their active component. These two medicaments are the subject of separate investigational new drug applications (IND's) with the FDA. If successful in their respective clinical trials, they will become the subject of separate new drug applications (NDA's). And ultimately, if they are approved by the FDA for commercial sale, they will be assigned distinct approval numbers indicative of the fact that they are distinct pharmaceutical products. Similarly, if the inventors were to elect to undertake clinical development of an intracorporeal photodynamic medicament, this would require filing of another IND and NDA since this third product would encompass a separate dosage form, route of administration, and intended use compared with either the topical photodynamic medicament or the injectable chemotherapeutic medicament.

Thus, any pharmaceutical product, including prescription or over-the-counter medicaments based on this disclosure, that are to be introduced into commerce in the U.S. or any other jurisdiction conforming to ICH standards, must contain certain elements, including proper labeling concerning intended use, that differentiates such product from any other product, despite any superficial similarities to such other product. Thus, such pharmaceutical product is not defined simply by its active ingredient, but rather by the combination of active ingredients and labeling claims (including intended use and dosage form). For example, a topically-applicable medicament (dosage form) for photodynamic therapy (intended use) containing rose bengal (active ingredient) is not rose bengal but rather a distinct pharmaceutical product containing rose bengal.

TABLE 1

Chemical, Physical and Photochemical Properties of Some Example Halogenated Xanthenes:

| | Substitution | | | | | | $\lambda_{max}$ (nm) | |
|---|---|---|---|---|---|---|---|---|
| Compound | X | Y | Z | $R^1$ | $R^2$ | MW (g) | $H_2O$ | EtOH |
| Fluorescein | H | H | H | Na | Na | 376 | 490 | 499 |
| 4',5'-Dichlorofluorescein | Cl | H | H | Na | Na | 445 | 502 | 511 |
| 2',7'-Dichlorofluorescein | H | Cl | H | Na | Na | 445 | 502 | 511 |

TABLE 1-continued

Chemical, Physical and Photochemical Properties of Some Example Halogenated Xanthenes:

| | | | | | | | | |
|---|---|---|---|---|---|---|---|---|
| 4,5,6,7-Tetrachlorofluorescein | H | H | Cl | H | H | 470 | 515 | |
| 2',4',5',7'-Tetrachlorofluorescein | Cl | Cl | H | Na | Na | 514 | 510 | 520 |
| Dibromofluorescein | Br | H | H | Na | Na | 534 | 504 | 510 |
| Solvent Red 72 | H | Br | H | H | H | 490 | | |
| Diiodofluorescein | I | H | H | Na | Na | 628 | 506 | 513 |
| Eosin B | $NO_2$ | Br | H | Na | Na | 624 | 522 | |
| Eosin Y | Br | Br | H | Na | Na | 692 | 517 | 523 |
| Ethyl Eosin | Br | Br | H | $C_2H_5$ | K | 714 | | 532 |
| Erythrosin B | I | I | H | Na | Na | 880 | 528 | 532 |
| Phloxine B | Br | Br | Cl | Na | Na | 830 | 541 | 548 |
| Rose Bengal | I | I | Cl | Na | Na | 1018 | 547 | 557 |
| Rose Bengal Dilithium | I | I | Cl | Li | Li | 986 | | 559 |
| Rose Bengal Amide | I | I | Cl | $C_2H_5$ | $(C_2H_4)_3NH$ | 1100 | | 563 |
| Rose Bengal Diamide | I | I | Cl | $(C_2H_5)_3NH$ | $(C_2H_4)_3NH$ | 1166 | | 559 |
| 4,5,6,7-Tetrabromoerythrosin | I | I | Br | Na | Na | 1195 | | |

| | $\lambda_{max}$ (nm) | $\alpha$ | $\phi$ (triplet) | $\phi$ (singlet oxygen) | | |
|---|---|---|---|---|---|---|
| Compound | MeOH | $(cm^{-1} \cdot mol^{-1} \cdot L)$ | MeOH | $H_2O$ | EtOH | MeOH |
| Fluorescein | 492 | $6.4 \times 10^4$ | 0.03 | 0.03 | 0.03 | 0.09 |
| 4',5'-Dichlorofluorescein | | | | 0.04 | 0.07 | |
| 2',7'-Dichlorofluorescein | | | | 0.04 | 0.07 | |
| 4,5,6,7-Tetrachlorofluorescein | | $2.9 \times 10^4$ | | | | |
| 2',4',5',7'-Tetrachlorofluorescein | | | | 0.05 | 0.05 | |
| Dibromofluorescein | | $1.4 \times 10^4$ | | 0.32 | 0.42 | |
| Solvent Red 72 | 450 | $1.4 \times 10^4$ | | | | |
| Diiodofluorescein | | $5.8 \times 10^4$ | | 0.33 | 0.48 | |
| Eosin B | | $3.9 \times 10^4$ | | | | |
| Eosin Y | 527 | $9.1 \times 10^4$ | 0.28 | 0.32 | 0.57 | 0.39 |
| Ethyl Eosin | | $1.1 \times 10^4$ | | | | |
| Erythrosin B | 529 | $9.1 \times 10^4$ | 0.62 | 0.69 | 0.63 | 0.62 |
| Phloxine B | 547 | $1.0 \times 10^5$ | | 0.40 | 0.63 | |
| Rose Bengal | 556 | $1.0 \times 10^5$ | 0.76 | 0.86 | 0.75 | 0.76 |
| Rose Bengal Dilithium | | | | | | |
| Rose Bengal Amide | | | | | | 0.74 |
| Rose Bengal Diamide | | | | | | 0.72 |
| 4,5,6,7-Tetrabromoerythrosin | | | | | | |

TABLE 2

Relative delivery efficacy of example transdermal delivery formulations of a halogenated xanthene; Rose Bengal is used as the agent at concentrations indicated by [RB]. The Formulation is applied to murine skin for 30 minutes under occlusive conditions. The Relative Efficacy indicates an estimate of the quantity of Rose Bengal delivered into the tissue, based on fluorescence measurement at the surface and in tissue cross sections. Depth indicates the relative depth of Rose Bengal penetration: LP = penetration to lamina propria; D+ = penetration to dermis and beyond.

| Formulation | | Relative | |
|---|---|---|---|
| [RB] | Vehicle | Adjuvant | Efficacy | Depth |
| 1% | Water | NaCl, 0.9% | HIGH | LP |
| 1% | Propylene Glycol | none | LOW | LP |
| 1% | Propylene Glycol | Lauric Acid, 5% | MED-HIGH | LP |
| 1% | Propylene Glycol | Oleic Acid, 5% | MED | LP |
| 1% | Propylene Glycol | Linoleic Acid, 5% | MED-LOW | LP |
| 1% | DMSO | none | VERY HIGH | D+ |
| 1% | Liquaderm-A | none | LOW | LP |
| 1% | Liqua-Gel | none | MED-HIGH | LP |

This description has been offered for illustrative purposes only and is not intended to limit the invention of this application, which is defined in the claims below.

What is claimed as new and desired to be protected by Letters Patent is set forth in the appended claims.

We claim:

1. A medicament adapted for topical administration, the medicament consisting of:
   a hydrophilic vehicle containing a halogenated xanthene, said halogenated xanthene corresponding in structure to Formula I

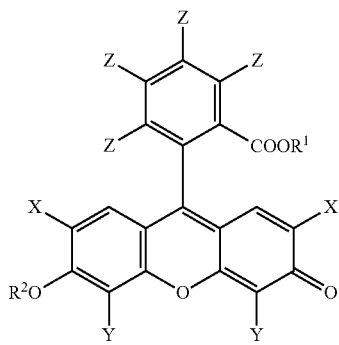

Formula I wherein $R^1$ is an ion selected from the group consisting of hydrogen ($H^+$), sodium ($Na^+$), potassium ($K^+$), calcium ($Ca^+$) and ammonium ($NH_4^+$);

wherein $R^2$ is an ion selected from the group consisting of hydrogen ($H^+$), sodium ($Na^+$), potassium ($K^+$), calcium ($Ca^+$) and ammonium ($NH_4^+$);

wherein X is selected from the group consisting of hydride, bromide, chloride, and iodide;

wherein Y is selected from the group consisting of hydride, bromide, chloride, and iodide; and wherein Z is selected from the group consisting of hydride, bromide, and chloride;

wherein said halogenated xanthene comprises disodium Rose Bengal;

said medicament containing:
said halogenated xanthene at a concentration of 0.001% to 0.01%;
at least one builder at a level sufficient to achieve a medicament viscosity in the range of 10-1000 cps; and
an electrolyte of sodium chloride, wherein the electrolyte is at a concentration of 0.9% or wherein the electrolyte is at a level sufficient to provide an osmolality of the medicament of 100 mOsm/kg to 500 mOsm/kg.

2. The medicament of claim 1 wherein said halogenated xanthene is at a concentration of 0.001%.

3. The medicament of claim 1 wherein said builder is selected from the group consisting of cellulose and cellulose derivatives, starch, alginates, and carboxymethylcelluloses and derivatives thereof, including those of medium to high viscosity, including USP carboxymethylcellulose.

4. The medicament of claim 1 wherein said builder is at a level sufficient to achieve a medicament viscosity in the range of 50-500 cps.

5. The medicament of claim 1 wherein said builder is at a level sufficient to achieve a medicament viscosity in the range of 75-250 cps.

6. The medicament of claim 1 wherein the osmolality is greater than 250 mOsm/kg.

7. The medicament of claim 1 wherein the osmolality of the medicament is in the range of 300-500 mOsm/kg.

8. The medicament of claim 1 wherein said hydrophilic vehicle consists of water.

9. The medicament of claim 1 wherein said medicament has a pH greater than approximately 4.

10. The medicament of claim 1 wherein said medicament has a pH in the range from 4-10.

11. The medicament of claim 1 wherein said medicament has a pH in the range from 5-9.

12. The medicament of claim 1 wherein said medicament has a pH in the range from 6-8.

13. The medicament of claim 1 wherein said medicament contains only, in a hydrophilic vehicle, at least one halogenated xanthene, a builder, and an electrolyte, and wherein said medicament has a pH close to physiologic pH.

14. The medicament of claim 1 wherein said medicament includes directions for usage as a topically-applicable medicament for photodynamic treatment, using activating light having an intensity of 25 mW/cm² or less, of human tissue.

15. The medicament of claim 1 wherein said medicament includes directions for usage as a topically-applicable medicament for photodynamic treatment of diseases of the skin and related organs.

16. The medicament of claim 1 wherein said medicament includes labeling that specifies the dosage form as a topically-applicable medicament, the intended use as photodynamic, therapy, and the active ingredient as Rose Bengal.

17. The medicament of claim 1 wherein said medicament includes labeling that specifies usage with ambient light activation, and the active ingredient as Rose Bengal.

18. The medicament of claim 1 wherein said medicament contains a microbial load of no more than 10 colony forming units per mL.

19. The medicament of claim 1 wherein said medicament is packaged in a light protective primary or secondary container.

20. A method of treatment of disease comprising topically applying to human or animal tissue a medicament comprising an aqueous halogenated xanthene saline solution wherein the halogenated xanthene comprises disodium Rose Bengal corresponding to the following formula:

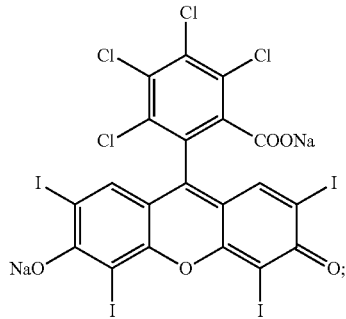

wherein said halogenated xanthene is present at a concentration of 0.001% to 0.01%; wherein the saline comprises water and an electrolyte of sodium chloride; wherein osmolality of the medicament is 100 mOsm/kg to about 500 mOsm/kg; wherein said medicament further comprises at least one builder at a level sufficient to achieve a medicament viscosity in the range of 10-1000 cps; and wherein said medicament is photoactivated using light having an intensity of 25 mW/cm² or less.

21. The method of claim 20 wherein said human or animal tissue comprises the skin and related organs, the mouth and digestive tract and related organs, the urinary and reproductive tracts and related organs, the respiratory tracts and related organs, other internal and external tissue surfaces, tissue surfaces exposed during surgery, and tissue with microbial or parasitic infection.

22. The medicament of claim 20 wherein the disease comprises hyperproliferative or inflammatory skin disorders.

* * * * *